United States Patent [19]
Digenis et al.

[11] Patent Number: 5,492,692
[45] Date of Patent: Feb. 20, 1996

[54] COATED PRODUCTS WITH POTENT ANTI-HIV AND ANTIMICROBIAL PROPERTIES

[75] Inventors: George A. Digenis, Lexington, Ky.; Alexander G. Digenis, Nashville, Tenn.

[73] Assignee: University of Kentucky Research Foundation, Lexington, Ky.

[21] Appl. No.: 229,090

[22] Filed: Apr. 18, 1994

Related U.S. Application Data

[63] Continuation-in-part of Ser. No. 106,948, Aug. 17, 1993, Pat. No. 5,380,523.

[51] Int. Cl.$^6$ .......................... A61K 47/32; A61K 31/085
[52] U.S. Cl. ...................... 424/78.25; 514/967; 514/843; 128/918
[58] Field of Search ............................... 424/78.24, 404, 424/433, 78.25; 514/967; 128/918

[56] References Cited

U.S. PATENT DOCUMENTS

| | | | |
|---|---|---|---|
| 4,954,351 | 9/1990 | Sackler et al. | 424/667 |
| 5,070,889 | 12/1991 | Leveen et al. | 128/830 |

OTHER PUBLICATIONS

Lancet 12/21 (1985/pp. 1422–1423 Hicks et al.
Simonelli et al. (1987) Proceed. of the 2nd Int. Symp. on Povidone Digenis et al. (1987) pp. 392–401.
Voeller, B. "Nonoxynol–9 and HTLV–III", *Lancet* (1986) 1153.
Malkovsky, M. et al, "Inactivation of HIV by Nonoxynol–9", *Lancet* (1988) 645.
Liebert, M. A. "Final Report on the Safety Assessment of nonoxynols –2, –4, –8, –9, –10, –12, –14, –15, –30, –40, and –50", *J. Am. Coll. Toxicol.* (1983) 2:35–60.
Chvapil, M. et al. "Studies on Nonoxynol–9. III. Effect on Fibroblasts and Spermatozoa", *Fertil. Steril.* (1980) 33:521–525.
Knaak, J. B. et al. "Excretion of Certain Polyethylene Glycol Ether Adducts of Nonylphenol by the Rat", *Toxicol. Appl. Pharmacol.* (1966) 9:331–340.
Walter, B. A. et al. "Disposition of [$^{14}$C] Nonoxynol–9 After Intravenous of Vaginal Administration to Female Sprague–Dawley Rats", *Toxicol. Applied Pharmacol.* (1988) 96:258–268.
Walter, B. A. et al. "High–Performance Liquid Chromatographic (HPLC) Analysis of Oligomeric Components of Spermicide Nonoxynol–9", *Pharm. Res.* (1991) 8:409–411.
Walter, B. A. et al. "Solubilization and *in Vitro* Spermicidal Assessment of Nonoxynol–9 and Selected Fractions Using Rabbit Spermatozoa", *Pharm. Res.* (1991) 8:403–408.
Higuchi, W. I. et al. "Drug Membrane Transport Enhancement Using High Energy Drug–Povidone Coprecipitates", *Proceedings of the International Symposium on Povidione, Digenis, G. A. and Ansell, J., Eds. Lexington, (1983) pp. 71–79.
Simonelli, A. P. et al. "Preparation and Evaluation of High Energy PVP–Coprecipitates Including Reversion Phenomena", *Proceedings of the 2nd International Symposium on Povidone*, Digenis, G. A. and Agha, B. J., Eds., Lexington, (1987) pp. 392–401.
Simonelli et al. "Dissolution Rates of High Energy Polyvinylpyrrolidone (PVP)–Sulfathiazole Coprecipitates", *J. Pharm. Sci.* (1969) 58:538–549.
Simonelli et al. "Dissolution Rates of High Energy Sulfathiazole–Povidone Coprecipitates II: Characterization of Form of Drug Controlling Its Dissolution Rate via Solubility Studies", *J. Pharm. Sci.* (1976) 58:355–361.
Mayersohn M. et al. "New Method of Solid–States Dispersion for Increasing Dissolution Rates", *J. Pharm. Sci.* (1966) 55:1323–1324.
Bird, K. D., "Editorial Review: The Use of Spermicide Containing Nonoxynol–9 in the Prevention of HIV Infection", *AIDS* (1991) 5:791–796.
Louv, W. C. et al. "A Clinical Trial of Nonoxynol–9 for Preventing Gonococcal and Chlamydial Infections", *J. Infect. Dis.* (1988) 158:518–523.
Niruthisard S. et al. "The Effects of Frequent Nonoxynol–9 Use on the Vaginal and Cervical Mucosa", *Sex. Transm. Dis.* (1991) 18:176–179.
LaRocca, R. et al. "Microbiology of Povidone–Iodine—An Overview", *Proceedings of the International Symposium on Povidone*, Digenis, G. A. and Ansell, J., Eds. Lexington, (1983) pp. 101–119.
Winicov, M. et al. "New Low Iodine Products Based on Stabilized Povidone–Iodine Solution", *Proceedings of the International Symposium on Povidone*, Digenis, G. A. and Ansell, J., Eds. Lexington, (1987) pp. 57–64.
Digenis, G. A. et al. "Studies on the Association of $^{14}$C–Povidone–$^{131}$I–Iodine Complex with Red Blood Cells and Bacterial Membranes", *Proceedings of International Symposium on Povidone*, Digenis, G. A. and Ansell, J., Eds. Lexington, (1983) pp. 302–311.
Ben–David A. et al. "The Protective Effect of Polyvinylpyrrolidone and Hydroxyethyl Starch on Noncryogenic Injury to Red Blood Cells", *Cryobiology* (1972) 9:192–197.
Berkelman, R. L. et al. "Increased Bactericidal Activity of Dilute Preparations of Povidone–Iodine Solutions", *J. Clin. Microbiol.* (1982) 15:635–639.
Polsky, Bruce, et al. "In Vitro Inactivation of HIV–1 by Contraceptive Sponge Containing Nonoxynol–9", *Lancet*, (1988) 1456.

*Primary Examiner*—Peter F. Kulkosky
*Attorney, Agent, or Firm*—Lowe, Price, LeBlanc & Becker

[57] ABSTRACT

A composition which has potent anti-HIV activity. The composition is a high energy coprecipitate of nonoxynol-9 oligomers, polyvinyl-pyrrolidone (PVP) and iodine or PVP-I and shows a pronounced synergistic, anti-HIV effect between the compounds of the composition. The invention also includes paper and plastic products coated with the composition of the invention.

23 Claims, No Drawings

COATED PRODUCTS WITH POTENT ANTI-HIV AND ANTIMICROBIAL PROPERTIES

This application is a continuation in part application of U.S. Ser. No. 08/106,948 filed Aug. 17, 1993, now U.S. Pat. No. 5,380,523.

TECHNICAL FIELD

I. The present invention relates to a composition with potent anti-HIV activity. The composition is a high energy coprecipitate of nonoxynol oligomers, polyvinylpyrrolidone (PVP) and iodine and shows a pronounced synergistic effect between the compounds of the composition.

II. The invention also relates to products coated with the high-energy coprecipitate composition, particularly to coated paper products, including surgical gowns and hospital linens.

III. The invention additionally relates to products coated with the high-energy coprecipitate composition, particularly to plastic products, including surgical gloves and prophylactics.

BACKGROUND

Nonoxynol or nonylphenol(polyethoxy)ethanol is a nonionic surfactant used as the active ingredient in the majority of the commercially available spermicides. It inhibits the in vitro growth of venereal pathogens (see Benes, S. et al., (1985) *Antimicrob. Agent Chemother.* 27: 724–726; Kelly, J. P. et al., (2985), *Antimicrob. Agent Chemother* 27: 760–762; Austin, H., et al., (2984) *JAMA,* 251: 2822–2824; and Singh, B. et al., (1972) *Br. J. Vener. Dis.* 48: 57–64), including the herpes simplex viruses (see Asculai, S. S. et al., (1978) *Antimicrob. Agent Chemother.* 13: 686–690; Hicks, D. R., (1985) *Lancet,* 1422–1423; Friedman-Kein, (1986) *J. Am. Acad. Dermol.* 15: 989–994; Rapp, R. et al., (1985) *Antimicrob. Agent Chemother.* 28: 449–451; Voeller, B., (1986) *Lancet,* 1153; Malkovsky, M. et al., (1988) *Lancet,* 645; and Barbi, M. et al., (1987) *Boll. 1st. Sieroter.* (Milan) 66: 158–160).

By the nature of its synthesis, the nonoxynol-9 (N-9) (Igepal CO-630) derivative of nonoxynol is a polymer consisting of at least 17 oligomers of varying ethylene oxide (EO) chain length. The molecule of N-9 contains a hydrophobic moiety (nonylphenol portion) and a hydrophilic chain composed basically of ethylene oxide units. The compound is a product of a statistical polymerization reaction of 9 moles of ethylene oxide and one mole of nonylphenol (see equation below):

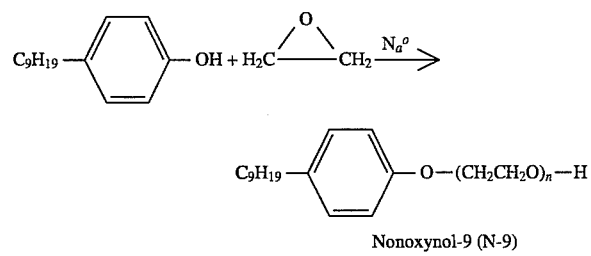

Nonoxynol-9 (N-9)

where "n" represents the number of ethylene oxide units.

The above reaction does not yield a distinct compound but a mixture of oligomers with different molecular weights. The physical and chemical characteristics of these oligomers change as a function of the varying molecular weight. (See Liebert, M. A., (1983) *J. Am. Coll. Toxicol.* 2: 35–60). As the length of the EO chain increases, the oligomers increase in water solubility. Nonoxynol-9 oligomers 1 through 6 (n=1–6) are considered oil soluble compounds, whereas the oligomers with a longer EO chain are soluble in water and polar organic solvents (see Liebert, supra).

These differences in chemical properties of N-9 oligomers affect their biological behavior both in vitro and in vivo. For instance, it was noted that the dermal toxicity of nonoxynol decreases as the molecular weight increases (see Liebert, supra) and that smaller molecular weight nonoxynol may be more toxic to fibroblasts than the larger ones (see Chvapil, M. et al., (1980) *Fertil. Steril.* 33: 521–525).

The in vitro spermicidal activity of the N-9 surfactant is also related to its molecular weight. Thus the oligomer n=9 when separated from the N-9 compound, was much more effective in inhibiting the motility of the spermatozoa than the higher molecular weight nonoxynols where n=30, 50, and 100. (See Chvapil, M. et al., (1980) *Fertil. Steril.* 33: 521–525.) The lower molecular weight nonoxynols (n=1 or 4) could not be studied appropriately because of their poor solubility in the aqueous testing medium (see Chvapil, supra).

Analogous dependence on molecular weight was observed in vivo. Oral absorption studies in the rat indicated that increasing the length of the ethylene oxide chain decreased N-9 oligomer intestinal absorption (see Knaak, J. B. et al., (1966) *Toxicol. Appl. Pharmacol.* 9: 331–340). Furthermore, data showed that absorption of N-9 through the vaginal membrane was poor and reflects the preferential absorption of lyophilic low molecular weight oligomers. (See Walter, B. A. et al. (1988) *Toxicol. Applied Pharmacol.* 96: 258–268.)

An efficient high pressure liquid chromatography (HPLC) method for the separation of [$^{14}$C] N-9 and characterization of the oligomeric components of the spermicide N-9 has been developed. (See Walter, B. A. et al. (1988) *Toxicol. Applied Pharmacol.* 96: 258–268; and Walter, B. A. et al., (1991) *Pharm. Res.* 8: 409–411).

Utilizing this normal phase gradient elution HPLC method, at least seventeen oligomers were isolated from commercial N-9. Selected oligomers representing the high, medium and low molecular weight fraction of N-9 were separated in milligram quantities by normal phase gradient HPLC (see Walter, B. A. et al., (1991) *Pharm. Res.* 8: 409–411; and Walter, B. A. et al., (1991) *Pharm. Res.* 8: 403–408).

Polyvinylpyrrolidone (also known as povidone USP) is one of the most highly utilized polymers in medicine because of its safety for human use and unique hydrophilic properties (see Robinson, B. V. et al. (1990), *A critical review of the Kinetics and Toxicology of Polyvinyl-pyrrolidone*, Lewis Publishers, Inc., Michigan).

Discovered and used during World War II as a plasma expander, PVP is currently used as excipient in many pharmaceutical preparations intended for external use (e.g. povidone-iodine USP solutions such as Betadine); for oral use, such as a solubilizing agent and tablet disintegrant, and for vaginal use such as in PVP-I douche.

Several studies have focused on the dissolution rate behavior of drug-povidone coprecipitates. (See Higuchi, W. I. et al., (1983) in *Proceedings of the International Symposium on Povidone*, Digenis, G. A. and Ansell, J., Eds. Lexington, pp. 71–79; Simonelli, A. P. et al., (1987) in *Proceedings of the 2nd International Symposium on Povidone*, Digenis, G. A. and Agha, B. J., Eds., Lexington, pp. 392–401; Simonelli et al., (1969) *J. Pharm. Sci.,* 58: 538–549; Simonelli et al. (1976) ibid. 65: 355–361.)

These studies found that the preferential dissolution of one component (hydrophilic polymer, such as PVP) can enhance the dissolution of the other component in a coprecipitate.

Drug/PVP high energy coprecipitates can be described as a drug incorporated into a solid PVP solution. Drug release from PVP coprecipitates are shown to follow dissolution kinetics of the polymer carrier of PVP provided that the PVP solvent uptake or swelling proceeds freely without inhibition by the drug.

Mayersohn and Gibaldi (Mayersohn M. et al., (1966) *J. Pharm. Sci.* 55: 1323–1324) showed greatly enhanced dissolution of the antibiotic griseofulvin when the drug was coprecipitated with povidone (PVP). Higuchi et al. investigated a povidone/sulfathiazole system and suggested that the resultant enhanced aqueous solubility of sulfathiazole was due to a high energy state of the drug in the PVP coprecipitate resulting in a supersaturated form of the drug after introduction into aqueous media. (See Higuchi, W. I. et al., (1983) in *Proceedings of the International Symposium on Povidone*, Digenis, G. A. and Ansell, J., Eds. Lexington, pp. 71–79.)

Simonelli et al., envisioned a PVP/drug coprecipitate model consisting of two components including the drug in amorphous state and PVP. (Simonelli, A.P. et al., (1987) in *Proceedings of the 2nd International Symposium on Povidone*, Digenis, G. A. and Agha, B. J., Eds., Lexington, pp. 392–401; Simonelli et al., (1969) *J. Pharm. Sci.* 58: 538–549; Simonelli et al. (1976) ibid. 65: 355–361.)

The in vitro spermicidal activity of three molecular weight fractions of N-9 were compared to that of N-9, using rabbit spermatozoa, at equimolar concentrations. nonoxynol-9/PVP complexes were found to be far more effective in immobilizing the sperm than either N-9 alone or in the separate fractions (Walter, B. A. et al., (1991) *Pharm. Res.* 8: 403–408).

The spermicidal activities of three oligomeric fractions of N-9 with human sperm have been assessed. Equimolar concentrations of three different molecular weight fractions of N-9 coprecipitated with PVP were used. These equimolar concentrations were 166 µg/ml for high molecular weight (HMW), (MW=599), 123 µg/ml for middle molecular weight (MMW) (MW=499) and 85 µg/ml for low molecular weight (LMW) (MW=306) N-9 fractions. The order of efficacy in immobilizing the human spermatozoa was HMW(MW=599)>MMW(MW=499)>LMW(MW=306) with complete sperm immobilization observed with PVP coprecipitated with N-9 HMW within 4.0 minutes and PVP coprecipitated with N-9 MMW within 15 minutes after exposure. Furthermore, addition of the spermicides interfered with the progressive motility and linearity of the sperm swimming pattern. PVP and buffer controls showed no decline in percentage motility over the course of the test.

Chvapil et al. recognized that the n=9 oligomeric fraction of nonoxynol-9 was more effective in inhibiting the motility of spermatozoa than the higher molecular weight nonoxynols. Chvapil et al., however, were unable to study the lower molecular weight oligomers (n=1–4) because of their poor solubility in aqueous media.

In contrast, however, Walter et al. were able to solubilize the water insoluble lower molecular weight N-9 oligomers by complexing them with the hydrophilic polymer polyvinylpyrrolidone (PVP). (See Walter, B. A. et al., (1991) *Pharm. Res.* 8: 403–408.)

The resulting high energy coprecipitate complexes of the low molecular species of N-9 were found to be at least effective spermicides at all concentrations tested when compared to their counterparts that were prepared from higher molecular weight N-9 oligomeric fractions. However, they were themselves effective spermicides. The above findings concluded that when N-9 is coprecipitated with PVP its spermicidal activity is enhanced. While PVP alone has no inherent sperm toxicity, the formation of N-9/PVP complexes seem to produce a synergistic response which causes a more rapid damage to the sperm than any of the two materials alone (Walter, B. A. et al., (1991) *Pharm. Res.* 8: 403–408).

Nonoxynol-9 (N-9) has been shownto be useful in the prophylaxis against sexually transmitted diseases (STD). (See Bird, K. D., (1991) AIDS 5: 791–796; and Louv, W. C. et al., (1988) *J. Infect. Dis.* 158: 518–523).

More recently, this spermicide has been shown to be effective against cell-associated HIV at concentrations of $\geq 0.05\%$ (v/v). (See Hicks, D. R. et al., (1985) *Lancet*, ii: 1422–1423; Vopeller, B., (1986) *Lancet*, i: 1153; and Malkovsky, M., Newell, A., Dalgleish, A. G., (1988) *Lancet*, i: 645).

Unfortunately, N-9 causes epithelial disruption of the cervix and vagina when administered in high doses and high frequency (see Niruthisard S. et al., (1991) *Sex. Transm. Dis.* 18: 176–179). Higher rates of new HIV infections were found in prostitutes who used N-9 at great frequencies (see Kreiss, J. et al., *International Conference on AIDS*, Montreal, June 1989 [Abstract MAO36]). This observation was attributed to the high incidence of genital ulceration caused by high doses of N-9, in this group of women. Thus, the above findings tend to suggest that novel spermicide formulations containing N-9 should be efficacious at the smallest possible doses so that the integrity of the vaginal epithelium is not compromised.

The antimicrobial properties of povidone-iodine (PVP-I), a complex of polyvinyl pyrrolidone and iodine, have been well documented. PVP-I solutions (10% w/v) USP are among the most widely utilized antimicrobial agents. A 10% (w/v) solution of PVP-I contains 1% (w/v) of available iodine ($I_2$). The microbiological potency of PVP-I arises from the elemental (diatomic) or free iodine ($I_2$) in solution. The significant characteristic of iodophors, such as PVP-I, is that they carry almost all of their iodine in a complexed formso that the amount of free iodine ($I_2$) is quite low and PVP-I serves as the iodine reservoir delivering the free iodine into the solutions. Thus, iodophors exhibit reduced irritation properties and are relatively non-toxic (see LaRocca, R. et al., (1983) in Proceedings of the International Symposium on Povidone, Digenis, G. A. and Ansell, J., Eds. Lexington, pp. 101–119).

Stable, sterile (0.2%) PVP-I compositions containing as little as 0.02% iodine have been shownto be useful in treating eye infections in humans. A level of 0.02% iodine obtained by diluting a commercial 10% PVP-I solution at 1:50 with saline solution, is generally considered to be optimum to maximize performance and minimize irritation (see Winicov, M. et al., (1987) in Proceedings of the International Symposium on Povidone, Digenis, G. A. and Ansell, J., Eds. Lexington, pp. 57–64).

Data has shown that with doubly labeled $^{14}C$-PVP-$^{131}I$ solutions the amount of iodine delivered into gram positive and negative bacteria cultures was three times greater when the iodine was complexed with PVP, than from an equimolar solution of $^{131}I_3^-$ (Lugol's solution). (See Digenis, G. A. et al., (1983) in Proceedings of International Symposium on Povidone, Digenis, G. A. and Ansell, J., Eds. Lexington, pp. 302–311).

The hydrophilic polymer PVP acts as a delivery system for iodine probably due to the membrane seeking properties of this polymer. Ben-David and Gavendo have shown that PVP at 4.6% w/v concentrations protect red blood cells from osmotic fragility and mechanical injury. (See Ben-David A. et al., (1972) *Cryobiology,* 9: 192–197). These workers suggested that this effect is brought about by a "coating" or external interaction of PVP with cell membranes.

The membrane-seeking properties of PVP suggest that in addition to its contribution to the solubilization ability of N-9, the PVP polymer, via its cell-membrane coating properties, also provides vaginal and cervical surface coverage coating with N-9 and iodine over extended periods of time.

In addition to its antimicrobial properties, PVP-I has been shown to inactivate HIV. (See Kaplan, J. C. et al. (1987) *Infect. Control* 8: 412–424; and Harbison, M. A. et al., (1989) *J. Acquir. Immune Defic. Syndr.* 2: 16–20). The concentration of iodine used in Kaplan's studies was equal to 0.025% for 250 ppm of $I_2$.

A 0.02% w/v (200 ppm) solution of iodine is considered non-toxic and non-irritating and is used for treatment of eye infections in humans. (See Winicov, M. et al., (1987) in *Proceedings of the International Symposium on Povidone,* Digenis, G. A. and Ansell, J., Eds. Lexington, pp. 57–64). In fact, the increased bactericidal activity of dilute solutions of povidoneiodine (Betadine - 10% w/v PVP-I) have recently been well documented. Betadine contains 10,000 ppm (or 10,000 µg/ml) of available iodine and is often irritating to the tissues and has an undesirable brown color. (See Berkelman, R. L. et al., (1982) *J. Clin. Microbiol.* 15: 635–639.) At concentrations of about 0.02% w/v of iodine, the undesirable brown color of iodine is not a problem since in dilute solutions the color is hardly seen and the amount of iodine is not irritating to tissues.

None of the prior research in this area recognized the synergistic anti-HIV result of all three compounds when formulated into a high energy coprecipitate.

Furthermore, spermicides containing nonoxynol-9 and polyvinylpyrrolidone or polyurethane are known.

U.S. Pat. No. 4,317,447 to Williams discloses a device for delivering a medicament to the vaginal cavity consisting of a molded sheath of a mixture of a polymeric material and a medicament. The medicament which is dispersed in the polymeric material can be nonoxynol-9. The polymer may be selected from modified cellulose, polyvinyl alcohol, polyvinylpyrrolidone, polyacrylic and ethylene oxide polymer. Williams does not disclose the use of PVP-I in combination with a nonoxynol-9.

U.S. Pat. No. 5,156,164 to LeVeen et al. discloses that iodine can be dissolved in alcohol containing nonoxynol in a complex with polyurethane. LeVeen et al. disclose that a polyvinylpyrrolidone-iodine complex has been effective in treating resistant vaginitis. LeVeen et al. do not disclose or suggest combining PVP-I with nonoxynol.

U.S. Pat. No. 5,070,889 to Leveen et al. discloses a contraceptive sponge and tampon made of polyurethane iodine complex. Leveen et al. teaches away from the use of povidone iodine or use as a contraceptive.

U.S. Pat. No. 5,073,365 to Katz et al. discloses clinical and personal care articles enhanced by lubricants and adjuvants. The devices can be made of polyvinylpyrrolidone or polyurethane interpolymers. The device may take the form of vaginal diaphragms, tampons, condoms or cervical caps. The medicament may be nonoxynol-9. Katz et al. disclose that the personal care articles may prevent the transmission of venereal diseases, possibly including AIDS.

U.S. Pat. No. 4,707,362 to Nuwayser discloses a sustained release composition made of synthetic polymers such as polyvinylpyrrolidone. The bioerodible material in one embodiment has been modified so that a spermicide such as nonoxynol-9 is slowly released. Nuwayser does not disclose PVP-I in combination with nonoxynol-9.

U.S. Pat. No. 4,954,351 to Sackler et al. discloses a method of producing standardized povidoneiodine preparations. The patent discloses that the povidone-iodine solution can be incorporated into a suppository with 0.1 to 10% by weight of povidone-iodine. Sackler et al. do not disclose the use of povidone-iodine in combination with nonoxynol-9.

U.S. Pat. No. 4,297,341 to Waller et al. discloses that a water-soluble complex comprising polyvinylpyrrolidone and gossypol is an effective spermicide. The patent discloses that a PVP-gossypol combination when compared to a comparative example of nonoxynol-9 alone, exhibited equal or greater spermicidal properties. Waller does not disclose PVP-I in combination with nonoxynol-9.

U.S. Pat. No. 4,925,033 to Stoner et al. discloses a microbicidal cleanser/barrier kit. One method of the invention involves applying a solution of povidone-iodine (PVP-I) to vaginal sponges or condoms. In another embodiment the povidone-iodine active ingredient may be added to spermicidal birth control compounds. Stoner et al. disclose that nonoxynol-9 is a known spermicidal compound. Stoner et al. do not disclose or suggest the particular combination of components in the form of a high energy coprecipitate, nor that the compounds show a synergistic anti-HIV effect.

Heterosexual transmission of human immunodeficiency virus (HIV), the causative agent of AIDS, is a growing concern in the United States where 37% of AIDS cases are heterosexually transmitted, the majority being male-tofemale. Moreover, the frequency of global heterosexual transmission is probably greater where it is estimated to exceed 60% of all AIDS cases.

It has been suggested that a major contributing factor to heterosexual transmission of HIV is the presence of cell-free virus and virus-infected cell (cell-associated virus) in genital secretions. Thus, vaginal contraceptives, which inactivate HIV should be an effective barrier to transmission.

The exposure to blood borne pathogens has always been of great concern to the community of individuals whose occupations require physical contact with tissue and body fluids and this concern has been heightened due to increase in the incidence of HIV. Current Occupational Safety and Health Administration (OSHA) standards regarding blood borne pathogens require the use of gloves in the processing and handling of any blood and/or body fluids.

There is a need in the pharmaceutical area for a paper products and plastic products coated with the antiviral composition of the invention.

The composition of the invention meets the above objectives and provides a high energy coprecipitate of nonoxynol-9 oligomers, polyvinylpyrrolidone and iodine (PVP-I). The composition shows a pronounced synergistic effect between the compounds which results in potent anti-HIV activity.

DISCLOSURE OF THE INVENTION

It is an object of the invention to provide a novel and potent composition possessing pronounced anti-HIV properties which is a high energy coprecipitate composition comprising N-9 oligomers and PVP and iodine. The PVP and iodine ingredients may be present in the coprecipitate composition as the complex PVP-I.

The invention further provides a high energy coprecipitate composition which is in the form of a powder. In a preferred embodiment the invention provides a high energy coprecipitate composition including PVP-I which comprises about 0.09–9% w/w of iodine.

In yet another embodiment, the invention provides a high energy coprecipitate composition of N-9 complexed with PVP comprising an antiviral concentration of free iodine of about 0.03% w/v or about 300 ppm.

The invention additionally provides a high energy coprecipitate composition of N-9 complexed with PVP comprising an antiviral concentration of free iodine providing about 9.4 to 0.09% $I_2$ providing an effective concentration of free iodine of 0.0094% w/v (94 ppm) and from about 11.8 –5.8% w/w of N-9 providing an effective concentration of N-9 of 0.0058% w/v (58 ppm).

In a further embodiment, the invention includes a high energy coprecipitate composition comprising an effective final concentration of from about 58 µg/ml–200 µg/ml of N-9.

The invention advantageously provides for a method of preparing a high-energy coprecipitate composition comprising the steps of:

(a) fractionating commercially available spermicide N-9 to seventeen oligomers by a preparative high pressure liquid chromatography (HPLC) procedure; and (b) converting the oligomers or commercially available N-9 to a high energy coprecipitate with PVP and iodine.

Preferred is a method of preparing a high-energy coprecipitate composition including the steps of:

(a) fractionating commercially available spermicide nonoxynol-9 (N-9) to seventeen oligomers by high pressure liquid chromatography (HPLC);

(b) adding an N-9 oligomer obtained in step (a) with a 10% or 1% solution w/v of PVP-I in a solvent, (c) placing the product of step (b) in an oil bath at about 100° C., and allowing the solvent to evaporate.

(d) obtaining a high energy coprecipitate of N-9, polyvinylpyrrolidone (PVP) and iodine.

Also included is a method of treating a female comprising administering to a female an effective amount of a high energy coprecipitate comprising N-9 oligomers, PVP and iodine to achieve a contraceptive and anti-HIV environment in the vaginal cavity. Thus, the invention provides spermicidal and anti-HIV activity with no irritation to the cervical and vaginal epithelia, and may take the form of an elegant, free flowing powder.

The invention advantageously provides paper and plastic products coated with the antiviral composition of the invention.

DESCRIPTION OF THE INVENTION

The present invention describes methodology for the preparation and assessment of new chemical entities with pronounced anti-HIV properties. These chemical entities incorporate N-9 or selected N-9 oligomers, small amounts of iodine ($I_2$) and the hydrophilic polymer PVP in such a way as to form high energy complexes, also known as coprecipitates.

The novel composition of the invention comprises a high energy coprecipitate made from N-9 oligomers, PVP and iodine. A pronounced synergistic effect is obtained between the compounds, enhancing the anti-HIV activity of the compounds when in the form of a coprecipitate. Due to the synergistic effect of the compounds present in the high energy coprecipitate, the coprecipitate requires less of each of the individual ingredients to achieve the desired anti-HIV result, than if the compounds were to be administered as a mixture. This is beneficial as it reduces irritation to tissues caused by higher doses of N-9 and iodine and thus reduces the potential for HIV virus transmission.

The high energy coprecipitates of the invention are formulated by fractionating commercially available spermicide, N-9, into seventeen oligomers by a preparative high pressure liquid chromatography (HPLC) procedure. Selected oligomers of N-9, or the commercially available N-9, are converted to high energy coprecipitates with PVP and various amounts of iodine (PVP-I). In a preferred embodiment the amount of iodine is about 0.09–9% w/w of iodine. The content of N-9 in the above complexes, in a preferred embodiment, ranges from 5.8–12% w/w.

N-9 and its oligomeric components are inherently viscous liquids which are converted to free flowing, water soluble powders by forming coprecipitates with PVP-I. Several combinations of iodine ($I_2$), N-9 and PVP are utilized to produce powders which exhibit a variety of spermicidal and anti-HIV activities.

In order to test and compare the anti-HIV activity of the high energy coprecipitates of the invention, the following assay procedure was performed.

Procedure for Anti-HIV Activity Assessment

High-titer suspensions (>$10^6$ infectious particles/ml) were incubated with each compound for 5 seconds, then immediately diluted 1:50 onto cultures of human MT-2 cells for detection of infectivity. Cellular toxicities were observed and no antiviral activities were expected after the 1:50 dilution, hence all antiviral activity would have resulted from the 5 second exposure. Infections were monitored by syncytium (giant cells) formation and Immune Fluorescence Assay (IFA). This assay utilizes an antiviral antibody with a fluorochrome attached to it through a covalent bond. Virus particles get to fluoresce when viable, and therefore the degree of infectivity is quantitated.

The results after 3, 5 and 8 days of incubation are shown in Table 1. In the control experiment, using the untreated virus, the MT-2 cells are 100% infected at the end of 3 days.

A 1% value or less, indicates a complete inactivation of the virus as measured by the IFA method, i.e. no fluorescent particles of the virus exist inside or outside the cells (Table 1).

Syncytia (giant cell) formation is assessed by staining techniques with subsequent microscopic examination. Syncytia formation indicates invasion of the MT-2 cells by the virus.

The method described is that of Montefiori et al. "Evaluation of Antiviral Drugs and neutralizing antibodies to human immunodeficiency virus by a rapid and sensitive microtiter infection assay", *J. Clin. Microbiol.* 1988, Vol 26: 231–235, incorporated herein by reference.

Table 1 summarizes the results of anti-HIV activity assessment of two high energy coprecipitate powders of PVP-I and N-9. The first was made with oligomers of N-9 with an average molecular weight of 599 and the second with the oligomers of N-9 with an average molecular weight of 306. Both samples were coprecipitated with PVP, iodine and one of N-9 oligomers mentioned above.

TABLE 1

Inactivation of Cell-Free and Cell-Associated HIV-1[1]

| DRUG | 3 days Syncytia | IFA[2] | 5 days Syncytia | IFA | 8 days IFA |
|---|---|---|---|---|---|
| 1a PVP (11.8 mg/ml) | +++ | >80% | CPE[3] | CPE | CPE |
| 1b PVP (0.236 mg/ml) | +++ | >80% | CPE | CPE | CPE |
| 2a PVP (3.24 mg/ml) high MW N-9 (0.2 mg/ml) | − | 10% | +++ | >80% | CPE |
| 2b PVP (0.0648 mg/ml) high MW N-9 (0.004 mg/ml) | +++ | >80% | CPE | CPE | CPE |
| 3a PVP (5.8 mg/ml) low MW N-9 (0.2 mg/ml) | − | 10% | +++ | >80% | CPE |
| 3b PVP (0.116 mg/ml) low MW N-9 (0.004 mg/ml) | +++ | >80% | CPE | CPE | CPE |
| 4a PVP-I (11.8 mg/ml) | − | <1% | − | <1% | 0% |
| 4b PVP-I (0.236 mg/ml) | +++ | >80% | CPE | CPE | CPE |
| 5a PVP-I (3.24 mg/ml) high MW N-9 (0.2 mg/ml) | − | <1% | − | <1% | 0% |
| 5b PVP-I (0.0648 mg/ml) high MW N-9 (0.004 mg/ml) | +++ | >80% | CPE | CPE | CPE |
| 6a PVP-I (5.8 mg/ml) low MW N-9 (0.2 mg/ml) | − | <1% | − | <1% | 0% |
| 6b PVP-I (0.116 mg/ml) low MW N-9 (0.004 mg/ml) | +++ | >80% | CPE | CPE | CPE |

[1]Details of experimental procedures are given in the test.
[2]% IFA positive cells
[3]CPE, viral-induced cytopathic effect was complete.
HMW N-9 = 599
LMW N-9 = 306
IPA = Imuno-flourescence assay The data in Table 1 show that PVP-I at a concentration of 11.8 mg/ml completely inactivated cell-free and cell-associated HIV-1. This represents approximately an effective concentration of 1.2% w/v of PVP-I or 0.12% w/v of free iodine (or 1,200 ppm of $I_2$).

A solution was made from a PVP-I and N-9 high energy coprecipitate. The coprecipitate composition was 94.2% w/w of PVP-I and 5.8% w/w of N-9, at a concentration of 3.24 mg/ml of PVP-I and 0.2 mg/ml of N-9 of an average molecular weight of 599. This composition achieved a complete eradication of the HIV virus in 30 seconds.

The use of high molecular weight N-9 oligomers as a component of the anti-HIV coprecipitate composition decreases the systemic absorption of N-9 and therefore N-9 is localized in the vagina and less toxic to the female.

Similar anti-HIV results were obtained with a coprecipitate of about 5.8 mg/ml PVP-I and about 0.2 mg/ml N-9 of an average molecular weight of 306. These results represent an antiviral concentration of free iodine of about 0.03% w/v (324 ppm). This level of iodine is not irritating to the vaginal epithelial tissue and desirably has no noticeable brown color.

In contrast to the above results, when no iodine is present in a coprecipitate composition made with 94.2% w/w of PVP and 5.8% w/w of N-9, at a concentration of 3.24 mg/mL of PVP and 0.2 mg/mL of N-9 of an average molecular weight of 599, the antiviral properties of the product were substantially reduced (see Table 1).

A similar reduction of the antiviral properties was also observed when the product was made from a PVP/N-9 high energy coprecipitate of 94.2% w/w of PVP and 5.8% w/w of N-9, at a concentration of 3.24 mg/mL of PVP and 0.2 mg/mL of N-9 of an average molecular weight of 599 (see Table 1).

Thus, in a preferred embodiment, the presence of 324 ppm iodine in the case of high molecular weight (599) N-9 and 580 ppm of iodine, in the case of the lower molecular weight N-9 (306) importantly adds to the synergistic anti-HIV effect of the high energy coprecipitate. The iodine and N-9 both act in a synergistic manner when complexed with PVP.

Other solutions made from PVP-I and N-9 coprecipitate in accordance with the invention include 94.2% of PVP-I and 5.8% of N-9 with an average molecular weight of 599. A further solution made from PVP-I and N-9 coprecipitate comprises 94.2% of PVP and 5.8% of N-9 with a weight average molecular weight of 306.

The chemical union of the iodine, PVP and several oligomers of the spermicidal agent N-9 with different molecular weights results in an impressive synergistic action of iodine and the spermicide N-9 against human immunodeficiency virus (HIV) (Tables 1 and 2).

The coprecipitate of the invention shows that the synergism between iodine and N-9 is of such magnitude that solutions with even smaller concentrations of these species can be used. Again, this is beneficial as it reduces vaginal irritation and thus reduces the potential for HIV virus transmission. Indeed, a complete eradication of the HIV-virus was obtained when coprecipitates of PVP, iodine and N-9 solution, containing as low as 58 ppm of N-9 and 940 ppm of PVP-I (94 ppm of iodine), were utilized (see Table 2).

TABLE 2

| Compound | Concentration on Virus [ug/mL = ppm] N9 | PVP-I | Syncytia % | IFA Position Cells % |
|---|---|---|---|---|
| No drug | — | — | 100 | 100 |
| KY048 | 58 | 940 | 0 | 0 |
| KY050 | 117.4 | 10 | 10 | 5 |

TABLE 2-continued

| | | | | | | | |
|---|---|---|---|---|---|---|---|
| KY052 | 118 | | 0 | | 30 | | 10 |

Composition of KY Coprecipitates

| | PVP | | PVP-I | | I$_2$ | | N-9 | |
|---|---|---|---|---|---|---|---|---|
| | % | ppm | % | ppm | % | ppm | % | ppm |
| KY048 | 0 | 0 | 94.20 | 940,000 | 9.40 | 94,000 | 5.80 | 58,000 |
| KY050 | 88.58 | 885,800 | 0.90 | 9,400 | 0.09 | 940 | 10.52 | 105,200 |
| KY052 | 88.20 | 882,000 | 0 | 0 | 0 | 0 | 11.8 | 118,000 |

The synergistic effect against the HIV is so significant that the above PVP-I/N-9 solution at concentrations as small as 58 ppm of N-9 and 94 ppm of iodine are effective, against the HIV virus (Table 2).

In addition to the unexpected synergism between the compounds, the coprecipitation of iodine, N-9 and PVP results in the formation of freely flowing powders which enable the preparation of elegant solid pharmaceutical formulations with control release properties. The coprecipitate powders are particularly useful in the design of acceptable solid formulations intended for vaginal, or other appropriate use.

The coprecipitate composition may be administered in the form of solid formulations, such as tablets or capsules, or as ointments, creams or suppositories. In a preferred embodiment the composition is administered in the form of a capsule or tablet.

Tablets, capsules, ointments, creams or suppositories may be formulated according methods known in the art such as those disclosed in *Remington's Pharmaceutical Science*, 18th Ed. pp. 1602–1712, incorporated herein by reference.

In contrast, N-9 by itself is a viscous liquid which cannot be formulated as a powder in solid dosage forms such as tablets or capsules. N-9 has heretofore been unable to form elegant tablets or capsules which are preferred by the user over creams and suppositories. Additionally, at its generally accepted effective spermicidal concentrations (approximately 160 mg/ml), N-9 is irritating to the vaginal epithelia and lining of the vaginal vault.

At concentrations below 550 ppm neither iodine nor N-9 are known to irritate sensitive membrane linings of the human body. Thus, the coprecipitate powders can be formulated into drug delivery systems that can release their active ingredients in a predictable manner without causing irritation to surrounding membrane linings.

The powders of the invention are acceptable to the user and furnish prolonged protection against AIDS and sexually transmitted diseases (STDs) with minimal absorption to the systemic circulation.

The main ingredient in the powders of the high energy coprecipitates, described in this invention, is the hydrophilic polymer PVP. This polymer, which exists in the powders in a ratio of approximately forty parts to one part of N-9, not only enhances the solubility of the various N-9 oligomers but also contributes to the synergistic action of N-9 and iodine against the AIDS virus. Thus, in a most important aspect of the invention, the active ingredients (N-9 and iodine) are present in the powder in such minuscule quantities that are known not to irritate membrane linings of the body.

The following examples are given to illustrate the invention, but are not to be construed as limiting.

EXAMPLE 1

The various compositions of coprecipitates are made according to the following general procedure: Stock solutions of approximately 1% w/v of PVP-I and 1% w/v N-9 are made in ethanol or methanol.

The N-9 stock solution is added dropwise to an aliquot of the PVP-I stock solution with stirring. It is critical that the two solutions are mixed at a very slow rate. Thus, the introduction of the N-9 solution, into the round bottom flask, containing the PVP-I, must be done dropwise but over a period of not longer than 1.5 hours.

Subsequently, the solvent is evaporated from the PVP-I/N-9 solution by heating in a preheated oil bath at 100° C. The temperature must be kept constant at 100° C. The evaporation process should last between 1–2 hours but no longer than two hours.

EXAMPLE 2

If a "glassy" coprecipitate is obtained following the general procedure described in example 1, diethyl ether is mixed with the residue. Upon evaporation of the diethyl ether a crystalline powder is obtained.

EXAMPLE 3

If a finely divided crystalline powder of the PVP-I/N-9 coprecipitate is desired, following the procedure described in Example 1, the residue, received after evaporation described in Example 1, is dissolved in a mixture of methanol/1,4 dioxane (1:4 ratio v/v) and subjected to freeze-drying for at least 12 hours. A fine crystalline powder is obtained by the freeze-drying step.

EXAMPLE 4

Commercially available nonoxynol-9 containing seventeen oligomers with an average molecular weight of 599 is utilized as a component in the general procedure described in Example 1. The oligomer of N-9 is isolated by the HPLC procedure disclosed in Walter, B. A. et al. (1988) *Toxicol. Applied Pharmacol.* 96: 258–268; Walter, B. A. et al., (1991) *Pharm. Res.* 8: 409–411; and Walter, B. A. et al., (1991) *Pharm. Res.* 8: 403–408, incorporated herein by reference).

Briefly, the separation is achieved by a preparative Zorbax-NH$_2$ column (250 mm, 7 μm×21.1 mm i.d.).

EXAMPLE 5

Stock solutions of N-9 (250 mg/ml) were prepared in tetrahydrofuran. A 1.0 ml aliquot was separated on a preparative Zorbax-NH$_2$ 7 μm column, 250 mm×21.2 mm I.D., using a linear solvent gradient from 98% A-2% B to 50% A-50% B in 90 min., where A=tetrahydrofuran:hexane (20:80, v/v) and B=water:2-propanol (10:90, v/v) delivered at 9.9 ml/min at ambient temperature and detection at 280 nm. The HPLC system used was a Waters HPLC system (Millipore, Waters Chromatography Division, Millford, Mass.) consisting of two Waters Moldel 510 HPLC pumps, a Waters Model 680 gradient controller, a Waters Model 440 Absorbance detector (280 nm), and a Waters Model SE120 dual channel recorder. Samples were introduced via a Rheodyne Model 7125 loop injector equipped with a 100 µl loop onto the HPLC column. Seventeen oligomers were collected, concentrated and reinjected onto the analytical system for further purification. The 599 molecular weight fraction and 305 molecular weight fraction were separated from the other fractions.

A 10% or 1% solution of w/v of PVP-I and the MW 599 fraction of the compound of nonoxynol-9 (N9) (isolated as set forth above) in absolute ethanol (methanol) was made. Both solutions were added via dropping funnels into a round bottom flask. It is important in this step to allow the dropping of the two solutions to continue for 1.5 hours. Thus the addition of the two solutions must take place slowly.

To an oil bath which had been preheated to 100° C., the flask was placed and the solvent allowed to evaporate. It was important to make sure that the temperature was well controlled during the evaporation process. The evaporation process should take between 1 and 2 hours. The evaporation should not take place longer than 2 hours.

A high energy coprecipitate of the compounds is obtained.

Examples 6–8 show formulations of the high energy coprecipitate of the invention.

EXAMPLE 6

A high energy coprecipitate composition of 9.4–0.09% I w/w and 11.8–5.8% N-9 w/w. The high energy coprecipitate provides anti-HIV protection at an effective concentration of about 3.24 mg/ml of PVP-I and 0.2 mg/ml of N-9 of an average molecular weight of 599 in a tablet formulation.

EXAMPLE 7

A high energy coprecipitate providing anti-HIV protection at an effective concentration of about 5.8 mg/ml PVP-I and 0.2 mg/ml N-9 of an average molecular weight of 305 in a capsule formulation.

EXAMPLE 8

A high energy coprecipitate providing anti-HIV protection at an effective concentration of about 58 ppm of N-9 and 940 ppm of PVP-I or 94 ppm of iodine in a cream formulation.

EXAMPLE 9

A multiple dose penile irritation study of the high energy coprecipitate composition of the invention identified below was conducted in the rabbit. The purpose of this study was to evaluate the potential for mucosal irritation of a solution administered to penile tissue. Animal treatment was begun and completed in seven days.

Materials: The high energy coprecipitate composition was identified and handled as follows:

Test Article:
  Spermicidal/anti-HIV agent
Storage Conditions:
  Controlled room temperature Vehicle:
  0.9% sodium chloride USP solution (SC)
Preparation:
  Following instructions provided, a 0.323 mg portion of the test article was solubilized in 100 ml of SC. The solution was kept refrigerated until use. Each dosing day, a sufficient amount of the test article solution was removed and brought to room temperature. The vehicle (SC) was dosed "neat" to serve as the control.
Condition of Extracts:
  SC Test: clear brown
  SC Control: clear
Methods
Animal Management:
  Five healthy male rabbits of the New Zealand White variety were obtained from USDA licensed suppliers. These animals were acclimated to the laboratory.

Rabbits, identified by ear tag or tattoo and weighing 2.5 kg to 2.6 kg, were individually housed in suspended cages and received a commercially pelleted rabbit feed on a daily basis; tap water was freely available. No diet or water analysis was performed since there were no contaminants suspected that could interfere with this study. Animal husbandry and environmental conditions conformed to current standard operating procedures which are based on the "Guide for the Care and Use of Laboratory Animals," NIH Publication No. 85–23.
Experimental Procedure
  Three rabbits each received a single 2.0 ml treatment of the high energy coprecipitate solution on each of 5 consecutive days. Two additional rabbits received a similar dose of the control vehicle. The appropriate test article solution or control vehicle was applied to the penis and surrounding prepuce. (Note: Not all of the test article solution or control vehicle remained in contact with the penile tissue.) Animals were maintained in restrainers for 4 hours and then returned to their respective cages.

Each animal was observed daily for general health. Rabbits were weighed just prior to first treatment and at study termination. The penile tissue was observed for signs of irritation the day following each application (prior to the next application) and also the day following last treatment in accordance with the following scoring scheme.

0=no change
  1=slight redness/or swelling
  2=moderate redness, slight swelling
  3=moderate redness and swelling
  4=marked redness and swelling Mucosal irritation was based on a comparison between test and control scores. Average irritation scores of 2 or greater were considered as slight irritation; scores of 3 or greater were considered as significant irritation.
Results
  Clinical Observations: All animals appeared clinically normal throughout the study
  Body Weight and Macroscopic Examinations:

| | Body Weight and Macroscopic Examination: | | |
|---|---|---|---|
| Rabbit | Weight (kg) | | |
| Number | Day 0 | Day 5 | Macroscopic Observations of Vagina |
| 75384 T | 2.4 | 2.4 | Macroscopically normal |
| 75303 T | 2.6 | 2.6 | Macroscopically normal |

-continued

Body Weight and Macroscopic Examination:

| Rabbit Number | Weight (kg) Day 0 | Day 5 | Macroscopic Observations of Vagina |
|---|---|---|---|
| 75296 T | 2.5 | 2.6 | Macroscopically normal |
| 75322 C | 2.5 | 2.6 | Macroscopically normal |
| 75302 C | 2.7 | 2.8 | Slight redness |

T = Test
C = Control

Evaluation

The average mucosal irritation scope for the test animals was 0 as compared to 0 for the control animals. There was no evidence of significant irritation in the test or control tissues of the rabbits.

Conclusion: Under the conditions of this study, the high energy coprecipitate composition was not considered an irritant to the penile mucosal tissues of the rabbit.

EXAMPLE 11

A vaginal irritation study of the high energy coprecipitate composition of the invention identified below was conducted in the rabbit. The purpose of the study was to evaluate the potential for mucosal tissue irritation of a material administered intravaginally to rabbits for 5 consecutive days. Animal treatment began and was completed within a 5 day period.

Materials: The high energy coprecipitate composition of the invention was identified and handled as follows:

Test article:
  Spermicidal/anti-HIV agent
Storage Conditions:
  Controlled room temperature
Control Article:
  0.9% sodium chloride USP solution (SC)
Preparation:
  A 0.323 mg portion of the test article was s olubilized in 100 ml of SC. The solution was kept refrigerated until use. Each dosing day, a sufficient amount of the test article solution was removed and brought to room temperature. The vehicle (SC) was dosed "neat" to serve as the control.
Condition of Solution:
  SC test solution: clear brown
  SC control: clear
Methods: Animal Management Five healthy female rabbits of the New Zealand White variety were obtained from USDA licensed suppliers. These animals were acclimated to the laboratory.

Rabbits, identified by ear tag or tattoo and weighing 2.4 kg to 2.7 kg, were individually housed in suspended cages and received a commercially pelleted rabbit feed on a daily basis; tap water was freely available. No diet or water analysis was performed since there were no contaminants suspected that could interfere with this study. Animal husbandry and environmental conditions conformed to current standard operating procedures which are based on the "Guide for the Care and Use of Laboratory Animals," NIH Publication No. 85–23.

Experimental Procedure:

Three rabbits each received a single 2 ml instillation of the high energy coprecipitate solution into the vagina for 5 consecutive days. Two additional rabbits received a similar dose of the control solution. The appropriate test article or control solution was introduced into the vaginal vault through a soft rubber catheter moistened with the preparation. Animals were returned to their cages after treatment.

Each animal was observed daily for general health and for external signs of irritation around the opening of the vaginal vestibule. Rabbits were weighed just prior to first treatment and at study termination.

On the day following the last treatment the rabbits were euthanatized by an intravenous injection of a sodium pentobarbital based euthanasia drug. Each vagina was removed in toto, opened longitudinally and examined macroscopically for signs of inflammation. Representative sections of each vagina were preserved in 10% neutral buffered formalin and histologically processed (hematoxylin and eosin stain) for microscopic evaluation by a board certified pathologist. The assessment for mucosal irritation potential was based on the histopathological findings.

Results and Clinical Observations: All animals appeared clinically normal throughout the study.

| Rabbit Number/Group | Weight (kg) DAY 0 | DAY 5 | OBSERVATIONS DAY 1 | DAY 2 | DAY 3 | DAY 4 | DAY 5 |
|---|---|---|---|---|---|---|---|
| 75333 Test | 2.6 | 2.5 | 0 | 0 | 0 | 0 | 0 |
| 75342 Test | 2.6 | 2.6 | 0 | 0 | 0 | 0 | 0 |
| 75337 Test | 2.5 | 2.6 | 0 | 0 | 0 | 0 | 0 |
| 75339 Control | 2.5 | 2.5 | 0 | 0 | 0 | 0 | 0 |
| 75360 Control | 2.6 | 2.6 | 0 | 0 | 0 | 0 | 0 |

Microscopic Evaluation: The average mucosal irritation score for the test animals was 5 as compared to 6 for the control animals. Individual results of the pathology findings appear in the attached microscopic evaluation.

Conclusion: Under the conditions of this study, the average mucosal irritation score of the vaginal tissues treated with the test article solution was within acceptable limits. The test article was not considered an irritant to the vaginal mucosal tissue of the rabbit.

II. PVP-I/N-9 coated paper products

The data set forth above shows that the chemical union of iodine, polyvinylpyrrolidone (PVP) and several oligomers of the spermicidal agent nonoxynol-9 (N-9) with different molecular weights results in an impressive synergistic action of iodine and the spermicide N-9 against human immunodeficiency virus (HIV) (Tables 1 and 2).

The coprecipitation of iodine, N-9 and PVP results in a synergism of such magnitude that very small concentrations of these chemical species posses good anti-HIV properties (Table 2). Indeed, complete eradication of the HIV-virus was obtained when such coprecipitates were used containing concentrations of PVP-I and N-9 of 940 ppm (94 ppm of iodine) and 58 ppm, respectively.

In addition to the unexpected synergism between the above chemical species, the coprecipitation of iodine, N-9 and PVP results in the formation of freely flowing powders which enable the preparation of elegant solid pharmaceutical formulations which otherwise would be very difficult to produce.

One application of the antiviral composition of the invention is the production of paper coated products or sheets of paper which possesses the ability to destroy the HIV virus instantly upon contact with biological fluids containing this virus. Such products, for example include, but are not limited to coated surgical gowns, paper masks, paper made bed covers and other paper liners utilized in hospital beds and on physician's examination tables. Any paper product can be coated with the high energy coprecipitate powder of the invention.

Exposure to blood borne pathogens has always been a primary concern for the community of individuals whose occupations require physical contact with tissue and body fluids. This concern has heightened due to the alarming increase in the incidence of Human Immunodeficiency Virus (HIV) infections. See Bartlett, J. G. "HIV Infection and Surgeons", *Current Problems in Surgery*, Wells, S. A., ed. Moseby-Year Book, Inc. 1992.

The community of concerned individuals is broad based and includes physicians, nurses, technical staff as well as ancillary personnel such as housekeeping staff. The Centers for Disease Control (CDC) has reported on 137 cases in which HIV was probably acquired through occupational exposure. 37 of these cases, which includes 4 surgeons have been strongly confirmed. The majority of these infections are thought to have occurred as the result of hypodermic or surgical needle punctures. See, CDC. "Recommendations for Assisting in the Prevention of Perinatal Transmission of Human T-Lymphotrophic Virus Type III/Lymphadenopathy-Associated Virus and Acquired Immunodeficiency Syndrome", *MMRW* 1985, 31:577–580.

In addition, the CDC has documented at least 3 healthcare workers who have acquired HIV through cutaneous or mucocutaneous contact. See, CDC, "Update: Human Immunodeficiency Virus Infection in Health-Care Workers Exposed to Blood Infected Patients", *MMRW* 1987, 36:19:285–289. Such transmission is thought to occur via breakdown in the integrity of cutaneous, mucocutaneous barriers with eventual exposure and infection of the host's immune cells. This type of transmission can occur from a myriad of sites including open cutaneous wounds, dermatitis with exudant, cuticular infections, etc.

The process of making the coated paper products of the invention is set forth below. The present invention broadly encompasses any paper product comprising an anti-HIV and antibacterial composition. In a preferred embodiment the paper product comprises anti-HIV and antibacterial composition which is applied to the paper product as a microencapsulated coating.

In a most preferred embodiment the anti-HIV and antibacterial composition is the high energy coprecipitate of PVPI/N-9. Mixtures of the drug (PVPI/N-9) were made and these were utilized as coating solutions (Tables 3 and 4). A thin layer of the drug was formed by spray-coating of the various solutions onto the paper.

Alternatively the paper may be coated by any coating process, including straight or roll coating procedures. The following coating methods may also be used.

COATING TECHNIQUES

1. Brush Coating
2. Roll Coating

Pressure

Kiss

Reverse Roll

3. Rod Coating
4. Knife Coating
5. Print Coating

Flexo

Gravure

6. Spray Coating

Cold Spray

Hot Spray

Electrostatic Spray

7. Dip Coating

For example, the high energy coprecipitate of the invention may be spray coated onto the paper material with a Binks spray gun model Mach 1 HVLP. When coating or spray coating, the high energy coprecipitate of the invention or other drug the "coat weight" (weight per unit area of "dry" non-volatile material which is applied to the paper substrate) is in the range of 2-30 g/m2 based upon 50–75% drug concentration in the coating. In a preferred embodiment the coat weight is in the range of 2–8 g/m2 based upon 50–75% drug concentration in the coating.

Other drugs which may be effective as anti-HIV and/or anti-bacterial materials may also be coated onto the paper material. These compounds include:

Acylclovir (Burroughs & Wellcome Corp.)—dose range: 200–1000 mg/cm$^2$.

Ribavirin (ICN Pharmaceuticals)—dose: about 20 mg/cm$^2$.

Retrovir (AZT) (Burroughs & Wellcome Corp.)—dose: 200–1500 mg/cm$^2$.

Interferon alfa-n3 (Purdue Frederick, Inc.)—dose: about 0.5 million I.U. (I.U.=International Units)

Chlorhexidine=antimicrobial agent (2–4%)

PVP-Bromine

In a preferred embodiment the coating material is the high energy coprecipitate PVP-I-N9 combination. Mixtures of the antiviral/antibacterial agents are also preferred.

When PVP-I-N9 coprecipitate is applied to the paper material a lower concentration of the drug is needed to be effective. A coat weight of 5.40 mg/cm$^2$ is more preferred when a PVP-I-N9 coprecipitate is applied to paper. A lower concentration of PVP-I-N9 coprecipitate translates to lower coat weights at 75% drug concentration or lower drug concentration or both.

Alternatively, any drug or the high energy coprecipitate can be attached to the surface of the paper by a microencapsulation process. Microencapsulation is the enclosure of an inner material, such as a drug, within an outer material processed into the form of microspheres in the micron size range of 0.1–1.50μ. The outer material which forms the microsphere is designed to be a protective coating and can be formulated with semipermeable membrane or slowly dissolving properties to achieve controlled release of the inner material.

One microencapsulation technique that can be used is dissolving the inner material in hydrophobic liquid and then forming an emulsion with a water soluble polymer with high speed mixing. Droplets of inner material in a hydrophobic liquid surrounded by microspheres of water soluble polymer are then formed.

Another microencapsulation technique. is heating a low-melting inner material to a molten state. This molten state material is then added to an aqueous solution of water soluble polymer forming an emulsion with high speed mixing. Droplets of molten inner material encased in microspheres of water soluble polymer are then formed. Microencapsulation solutions can be coated on a variety of substrates with conventional coating techniques. In a preferred embodiment a drug or the high energy coprecipitate composition is microencapsulation coated onto the paper material.

Tables 3 and 4 describe preferred embodiments of the components utilized for film coating solutions and examples of their compositions, respectively.

In a preferred embodiment the coated-paper was prepared as follows: Paper taking the form a commercial surgical paper gown was sprayed by a solution of the PVP-I/N-9 (drug) in ethanol-water (8:1).

The composition of coating solution is represented by example D of Table 4 and was as follows: Drug (PVP-I/N-9) 75% w/w; HPMC 6% w/w; PEG 1450 14% w/w; talc 15% w/w and Tween 80–6% w/w.

The final concentration of the total amount of drug on the paper was found by titration of iodine (using the United States Pharmacopeia) to be 4.05 mg/cm$^2$. Of this amount 0.375 mg is iodine, 0.25 mg is N-9 and the remaining (3.43 mg) is PVP. As little as 0.5 mg/cm$^2$ of the drug (PVP-I/N-9) is needed to kill completely the virus ($1\times10^5$ infectious, cell-free virus particles per 0.1 ml of contaminated blood).

If one considers that approximately one to two drops of blood (0.05–0.1 ml) are to be absorbed per square centimeter (cm$^2$) of the coated paper. Table 1 shows approximately 300 μg of the drug are needed to kill the virus in 0.1 ml of blood. Thus, if 1 cm$^2$ of paper absorbs two drops of blood (0.1 ml), the effective amount of antiviral compound required per cm$^2$ of paper is about 0.3 mg/cm$^2$–about 0.6 mg/cm$^2$.

Film coating solutions may contain polymers, colorants, glidants, plasticizers, and vehicles known to those of skill in the art.

The following tables provide examples of the components of the coating solutions for paper coated products of the inventions.

TABLE 3

| COMPONENTS FOR FILM COATING SOLUTIONS |
|---|
| POLYMERS: |
| 1. Hydroxypropyl Methyl Cellulose (HPMC) |
| 2. Hydroxypropyl Methyl Cellulose Phthalate (HPMCP) |
| 3. Hydroxypropyl Cellulose (HPC) |
| 4. Hydroxypropyl Methyl cellulose Acetate Succinate (HPMCAS) |
| 5. Eudragit RS PO* |
| 6. Eudragit RL PO* |
| 7. Eudragit E 100* |
| 8. Polyethylene glycol (PEG 1450, PEG 8000, PEG 6000) |
| 9. Ethyl Cellulose (EC) |
| COLORANTS: |
| 1. Titanium dioxide |
| 2. Aluminum lake |
| 3. Red iron oxide |
| 4. Dyes |
| PLASTICIZERS: |
| 1. Glycerin |
| 2. Propylene glycol |
| 3. Polyethylene glycol |
| 4. Triacetin |
| 5. Triethyl citrate |
| 6. Diethyl phthalate |
| 7. Dibutyl phthalate |
| GLIDANTS: |
| 1. Talc |
| 2. Magnesium stearate |
| VEHICLES: |
| 1. Alcohols |
| 2. Ketones |
| 3. Esters |
| 4. Chlorinated hydrocarbons |
| 5. Water |

*Note:
PO means powder supply
100 means granulate supply
Eudragit RL - copolymer of acrylic and methacrylic acid esters with low content of quaternary ammonium groups.
Eudragit E - copolymer of dimethyl aminoethyl methacrylate and neutral methacrylic acid ester.

Table 4 below includes some examples of preferred embodiments of the coating solutions of the invention.

TABLE 4

| EXAMPLES OF COATING SOLUTIONS | |
|---|---|
| A | |
| antiviral composition | 50–75% |
| HPMCAS | 10–20% |
| Triethyl citrate | 2.8–5.0% |
| Talc | 3.0–7.0% |
| Water/Ethanol | (20:80)% |
| B | |
| antiviral composition | 50–75% |
| HPMCP | 6–20% |
| Methylene chloride/Ethanol | (1:1) |
| C | |
| antiviral composition | 50–75% |
| HPMC | 6–20% |
| PEG 6000 | 12–25% |
| EC or HPMCP | 5–15% |
| Methylene chloride/ethanol | (1:1) |
| D | |
| antiviral composition | 50–75% |
| HPMC | 6–10% |
| REG 1450 | 9–25% |
| Talc | 7–10% |
| Tween 80 | 5–7% |
| Water/ethanol | (8:1) |
| E | |
| antiviral composition | 50–75% |
| Eudragit RL PO or Eudragit RS PO | 10–15% |
| PEG 6000 | 12–25% |
| Talc | 7–10% |
| Tween 80 | 5–7% |
| Water/ethanol | (7:3) |
| F | |

TABLE 4-continued

EXAMPLES OF COATING SOLUTIONS

| | |
|---|---|
| antiviral composition | 50–75% |
| Eudragit E 100 | 5–10% |
| PEG 6000 | 12–25% |
| Talc | 7–10% |
| Tween 80 | 5–7% |
| Water/ethanol | (2:8) |

Coating solutions may be applied to the surface of the any paper product or between plys of the paper products.

ANTI-HIV STUDY

A study was conducted to test the anti-HIV properties of paper materials coated with the anti-HIV compound of the invention.

Tests were performed by placing 0.5 ml of virus (HIV-1111B), >$10^6$ infectious particles/ml) in the center of an area of a surgical gown which had been treated with the anti-HIV PVP-I/N-9 high energy coprecipitate compound of the invention. The drop of virus was swirled until it covered an area of approximately 2 inches in diameter. After a 2 minute incubation, 50 ul of the virus suspension was removed from the treated area of the surgical gown and diluted in 1:100 in growth medium. Fifty microliters of diluted virus was then added to 200 ul of MT-2 cells in a 96-well plate. Infections were monitored by syncytium (giant cell) formation, immunofluorescence assay (IFA) and p24 assay for a period of 11 days. As a separate control, the original virus suspension was tested before adding it to any materials (i.e. untreated virus). In addition, an untreated gown was tested which was not treated with PVP-I/N-9 high energy coprecipitate.

Results: Untreated virus and virus placed on control gown fabric produced syncytia and complete cell killing after 5 days of incubation with MT-2 cells. Virus that had been placed on both of the treated gown fabrics produced no syncytia after 11 days, and all the cells were negative by IFA and p24 assay for viral antigen synthesis, indicating that all infectious viral particles had been inactivated. Thus, the treated paper products inactivate HIV virus and provide a barrier to HIV virus.

III. PVP-I/N-9 coated plastic products

In accordance with the present invention, it is also desirable to coat plastic, polymer or latex products with the antiviral/antibacterial compound of the present invention. Any plastic product may be covered with the antiviral powder of the invention, including, for example, plastic gloves, including surgical gloves and latex condoms, including male and female condoms.

Current Occupational Safety and Health Administration (OSHA) standards regarding blood borne pathogens requires the use of gloves in the processing and handling of any blood and/or body fluids. These standards are continually being reviewed and the development of additional safety and protection devices are being investigated. These include devices or barriers that contain antiviral compounds.

A study was performed to evaluate the dermatologic tolerance of the antiviral powder of the invention when used as an antiviral barrier worn topically inside surgical and medical gloves. The study examined the dermatologic allergenic properties of the powdered compound when worn by individuals for extended periods of time. The results of the study are equally applicable to safety of condoms coated with the antiviral composition of the invention.

A blinded study was designed to address the irritability of antiviral powder of the invention when utilized as a topical agent on the epidermis of the hand. Dermatologic contact was achieved via the use of commercially available, nontreated latex surgeon's gloves to which 250 milligrams of antiviral powder was applied to the inner surface of either the right or left glove. The remaining gloves remained untreated.

The study population consisted of 25 healthy volunteers. Males or females between the ages of 18–75 years who will be recruited for this study. Only individuals with no existing rashes, eczema, abrasions, cuts or dermatologic abnormalities were included in the study.

Control gloves and treated gloves were provided to the volunteers. Distribution and collection of the gloves prior to and after exposure was coordinated by the principal investigator. Each treatment glove (latex or nylon) had approximately 250 mg of antiviral powder added to the inside lining.

In keeping with current standards and providing additional barriers for protection of healthcare workers, a sample of PVP-I/N-9 containing 940 ppm of $I_2$ and 62,000 ppm of N-9 was prepared which was placed in latex surgical gloves for use as additional protection to be used in medical treatment, and in surgical and handling procedures.

Antiviral compound was in powder form and of the same consistency of commercially available glove talc or corn starch. Control gloves were of the same material (latex or nylon) and were not treated with any additives.

At the conclusion of the study all materials including exposed gloves were returned. Clinical assessment of each volunteer was made by a board certified dermatologist.

Each volunteer was examined by the physician immediately prior to exposure and was assessed for any pre-existing dermatologic condition. Once the physician has assessed the volunteers' dermatologic condition and determined that no pre-existing condition existed, the volunteer were allowed to initiate the study. Photographs (135 mm, 100ASA) were made of each hand on both the dorsal and ventral surface of each volunteer. Volunteer codes and dates were included in the photographs.

Volunteers' dermatologic condition were assessed by the physician at seven day intervals during the exposure period and at the end of a seven day period following the exposure period. Each volunteers' hands were photographed immediately following the 21 day exposure period in the same fashion as described above. All clinical assessments were accompanied by written evaluations of the physician.

Any abnormal dermatologic condition such as itching, eczema, swelling, numbness or any other abnormality experienced by the volunteer was required to be reported to the principal investigator immediately and any such volunteer was withdrawn from the study. Clinical assessment and evaluation by the physician was made within 24 hours. Photographs were made of the volunteers hands, as described earlier, for documentation.

An assessment was performed of the dermatologic safety and allergenic properties of the antiviral powder with specific kill properties for the human immunodeficiency virus.

Each volunteer was examined by the physician immediately prior to exposure for detection of any preexisting dermatologic condition. Twenty-five human volunteers, 16 male, 9 female with average age of 36 years, were exposed to 250 mg of the compound contained in powder free examination gloves. Powder free examination gloves without the antiviral agent was worn on the opposite hand and served as a control.

Gloves were worn by the individuals for 4 hours/day for 21 consecutive days. Dermatologic examinations were performed at 7 day intervals. Results: All 25 subjects completed the 21 day exposure period with a total exposure time of 2,224 hours (Table 5). Average exposure time per day was 4.21 hours with the greatest exposure being 5.24 hours/day (Table 5). Dermatologic evaluations revealed no allergenic or abnormal dermatologic conditions arising from the exposure to the antiviral compound. Two subjects were reported to have known dermatologic reactions with commercially available gloves treated with talc or cornstarch. Examinations from these subjects were negative.

It was concluded that the use of an antiviral compound designed for the use in surgical, examination or handling gloves as an antiviral barrier was shown not to cause any dermatologic reactions or abnormalities to the hands. The PVP-I/N-9 drug will provide an additional effective and safe barrier for individuals whose occupations require the physical contact with human tissue and/or body fluids. This group of individuals is not limited to but includes physicians and surgeons, nurses and ancillary personnel such as housekeeping personnel.

TABLE 5

HAND IRRITABILITY ASSESSMENT OF THE ANTIVIRAL POWDER (PV-I/N-9) IN HUMAN VOLUNTEERS

| | |
|---|---|
| TOT. NO. of MALE SUBJ. | 16 |
| TOT NO. of FEMALE SUBJ. | 9 |
| AVG. AGE of SUBJ. | 36 |
| S.D. of AGE | 13 |
| OLDEST SUBJ. | 62 |
| YOUNGEST SUBJ. | 18 |
| AVG. AGE of MALE SUBJ. | 35 |
| S.D. of MALE SUBJ. AGE | 14 |
| OLDEST MALE SUBJ. | 61 |
| YOUNGEST MALE SUBJ. | 18 |
| AVG. AGE of FEMALE SUBJ. | 38 |
| S.D. of FEMALE SUBJ. AGE | 12 |
| OLDEST FEMALE SUBJECT | 62 |
| YOUNGEST FEMALE SUBJ. | 19 |
| TOT. NO. OF EXP. HRS | 2224 |
| TOT. NO. OF EXP. DAYS | 528 |
| AVG. EXP. per SUBJ. (Hr.) | 88.96 |
| AVG. EXP./SUBJ./DAY (Hr.) | 4.21 |
| LONGEST EXP. (HR.) | 110 |
| SHORTEST EXP. (HR.) | 84 |
| LONGEST EXP. (DAY) | 23 |
| SHORTEST EXP. (DAY) | 20 |
| LONGEST AVG. EXP./DAY | 5.24 |
| LEAST AVG. EXP./DAY | 4.00 |

Thus, the plastic products of the invention advantageously, provide protective, non-irritating antiviral barriers for use in the work place, hospital, home and wherever antiviral and antibacterial barriers are required. The plastic product generally incorporated an anti-HIV and antibacterial composition. These compounds include:

Acylclovir (Burroughs & Wellcome Corp.)—dose range: 200–1000 mg/cm$^2$.

Ribavirin (ICN Pharmaceuticals)—dose: about 20 mg/cm$^2$.

Retrovir (AZT) (Burroughs & Wellcome Corp.)—dose: 200–1500 mg/cm$^2$.

Interferon alfa-n3 (Purdue Frederick, Inc.)—dose: about 0.5 million I.U. (I.U.=International Units)

Chlorhexidine=antimicrobial agent (2–4%)

PVP-Bromine

In a preferred embodiment the anti-HIV and antibacterial composition is applied to the plastic product as a coating. In a most preferred embodiment the anti-HIV/antibacterial compound is the PVP-I/N9 compound of the invention.

The invention is not to be limited to the exact details of operation, or to the exact compositions, methods, procedures, products or embodiments shown and described, as obvious modifications and equivalents were apparent to one skilled in the art. The invention is therefore to be limited only by the full scope which can be legally accorded to the appended claims. All publications cited herein, are incorporated herein by reference in their entirety.

We claim:

1. A coated paper product comprising a paper product coated with a high energy coprecipitate of nonoxynol oligomer and polyvinyl pyrrolidone polymer and iodine, or nonoxynol oligomer and polyvinylpyrrolidone-iodine complex (PVP-I), wherein the combined effect of the compounds simultaneously precipitated in said high energy coprecipitate exceeds the individual effect of said compounds, and wherein said high energy coprecipitate has antiviral activity against human immunodeficiency virus-1 (HIV-1) in an MT-2 assay.

2. The product of claim 1, wherein in said paper product is selected from the group consisting of surgical gowns, paper masks, paper-made bed covers, and paper liners utilized in hospital beds and physician's examination tables.

3. The product of claim 1, wherein said high energy coprecipitate composition is coated on said paper product by a coating method selected from the group consisting of brush coating, roll coating, pressure coating, kiss coating, reverse roll coating, rod coating, knife coating, print coating, flexo coating, gravure coating, spray coating, cold spray coating, hot spray coating, electrostatic spray coating, dip coating, and microencapsulation coating.

4. The product of claim 3, wherein said high energy coprecipitate composition is sprayed onto said paper product in the form of a coating comprising 50–75% by weight antiviral composition, 6–10% polymer by weight, 9–25% by weight plasticizer, and 7–10% by weight filler.

5. The product of claim 1, wherein said high energy coprecipitate composition is applied to said paper product as a microencapsulated coating.

6. The product according to claim 1, wherein said coprecipitate is a powder.

7. The product according to claim 6, wherein said powder is a finely divided crystalline powder.

8. The product according to claim 1, wherein said PVP-I comprises about 0.09–9.4% w/w of iodine.

9. The product according to claim 1, wherein said PVP-I comprises an antiviral concentration of free iodine of about 0.03% w/v or 300 ppm complexed with PVP.

10. The product according to claim 1, wherein said PVP-I comprises an effective antiviral concentration of free iodine of about 0.0094 w/v of iodine or 94 ppm complexed with PVP.

11. The product according to claim 1, wherein said nonoxynol oligomer of said coprecipitate comprises from about 5.8 to 11.8% w/w of nonoxynol-9 oligomer.

12. The product according to claim 1, wherein said coprecipitate is present at a concentration of about 3.24 mg/ml of PVP-I and about 0.2 mg/ml of N-9 oligomer of an average molecular weight of 599.

13. The product according to claim 1, wherein said coprecipitate is present at a concentration of about 5.8 mg/ml PVP-I and about 0.2 mg/ml N-9 oligomer of an average molecular weight of 306.

14. The product according to claim 1 wherein said coprecipitate is present at a concentration of about 5.8 ppm of N-9 oligomer and about 940 ppm of PVP-I or 94 ppm of iodine.

15. The product according to claim 1, wherein said nonoxynol oligomer is an nonoxynol-9 oligomer with an average molecular weight of 599.

16. The product according to claim 1, wherein said nonoxynol oligomer is nonoxynol-9 oligomer comprising oligomers of N-9 having a range of molecular weight of each oligomer from about 264 to about 1000.

17. The product according to claim 1, wherein the percent of polyvinyl pyrrolidone ranges from about 88% to about 97%.

18. The product according to claim 1, wherein the average molecular weight of said polKvinyl pyrrolidone ranges from about 2,500 to 1,100,000.

19. A paper product coated with an anti-HIV and antibacterial composition.

20. The product of claim 19, wherein said anti-HIV and antibacterial composition is applied to said paper product as a microencapsulated coating.

21. The product of claim 19, wherein said anti-HIV and antibacterial composition is applied to said paper in the form of a coating with a coat weight of 2–30 g/m$^2$ based upon a 50–75% anti-HIV and antibacterial composition concentration in the coating.

22. A coated plastic product comprising a plastic product coated with a high energy coprecipitate of nonoxynol oligomer and polyvinyl pyrrolidone polymer and iodine, or nonoxynol oligomer and polyvinylpyrrolidone-iodine complex (PVP-I), wherein the combined effect of the compounds simultaneously precipitated in said high energy coprecipitate exceeds the individual effect of said compounds, and wherein said high energy coprecipitate has antiviral activity against human immunodeficiency virus-1 (HIV-1) in an MT-2 assay.

23. The product of claim 22, wherein said plastic product is selected from the group consisting of gloves, plastic liners, and condoms.

* * * * *